United States Patent [19]

Marhold et al.

[11] Patent Number: 5,484,953
[45] Date of Patent: Jan. 16, 1996

[54] O-PHENYLENEDIAMINES CONTAINING FLUOROALKYL(ENE) GROUPS

[75] Inventors: Albrecht Marhold, Leverkusen; Bernd Baasner, Bergisch Gladbach; Folker Lieb, Leverkusen, all of Germany

[73] Assignee: Bayer Aktiengesellschaft, Leverkusen, Germany

[21] Appl. No.: 253,466

[22] Filed: Jun. 3, 1994

Related U.S. Application Data

[62] Division of Ser. No. 145,428, Oct. 29, 1993.

[30] Foreign Application Priority Data

Nov. 6, 1992 [DE] Germany ............... 42 37 564.9

[51] Int. Cl.$^6$ .......... C07D 319/14; C07C 209/36; C07C 211/52; C07C 233/43
[52] U.S. Cl. .......... 549/362; 548/302.1; 558/418; 560/9; 560/13; 560/30; 564/218; 564/221; 564/223; 564/406; 564/407; 564/416; 564/417; 564/418; 564/419; 564/440; 564/442
[58] Field of Search ............ 549/362; 548/302.1

[56] References Cited

U.S. PATENT DOCUMENTS 4,581,466  4/1986  Marhold .................. 549/359
4,767,444  8/1988  Heywang et al. .......... 548/302.1

OTHER PUBLICATIONS

Ullmann's Encyclopedia of Industrial Chemistry, Fifth Edition, vol. A 11: Fibers, 5. Synthetic Inorganic, to Formaldehyde (1988).

*Primary Examiner*—Peter O'Sullivan
*Attorney, Agent, or Firm*—William C. Gerstenzang; Sprung Horn Kramer & Woods

[57] ABSTRACT

Novel o-phenylenediamines of the formula containing fluoroalkyl(ene) groups

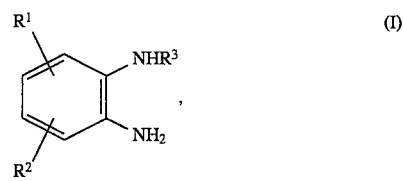

in which the symbols used have the meaning given in the description, processes for their preparation and their use as intermediates.

1 Claim, No Drawings

O-PHENYLENEDIAMINES CONTAINING FLUOROALKYL(ENE) GROUPS

This is a division of copending application Ser. No. 08/145,428, filed Oct. 29, 1993.

EP-A2-251,013 and EP-A1-487,286 describe o-phenylenediamines which are different from those which form the subject matter of the present invention.

The present invention relates to o-phenylenediamines of the formula (I) containing fluoroalkyl(ene) groups

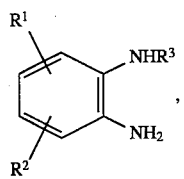

in which $R^1$ represents $CF_3$, $OCF_3$, $SCF_3$, $SO_2$—$C_1$—$C_6$—alkyl, which can be straight-chain or branched and be substituted completely or in part by fluorine, $N(CF_3)_2$, a phenyl or phenoxy radical containing $CF_3$ or CN in the 4 position and, if desired, further substituents, 1,1,2,3,3,3-hexafluoropropoxy, 1,1,2-trifluoro-2-chloroethoxy, 1,1,2,2-tetrafluoroethoxy, 1,1,2-trifluoro-2-chloro-ethylthio or 1,1,2,3,3,3-hexafluoropropylthio, independently thereof $R^2$ represents F, Cl, Br, CN, $CH_3$, $OCF_3$, $SO_2$—$C_1$—$C_6$—alkyl, which can be straight-chain or branched and substituted completely or in part by fluorine, COO—$C_1$—$C_6$—alkyl, $COOC_6H_5$, 1,1,2,2-tetrafluoroethoxy, 1,1,2,3,3,3-hexafluoropropoxy or 1,1,2-trifluoro-2-chloro-ethoxy, and $R^3$ represents hydrogen, $COCH_3$ or $COCF_3$, it being possible for $R^1$ and $R^2$ together to represent an —O—CFCl—CFCl—O— radical, with the exception of the compounds described in EP-A 251,013 and EP-A 487,286.

Preferred o-phenylenediamines of the formula (I) containing fluoroalkyl groups contain the following radicals $R^1$ and $R^2$ in the position given in each case, $R^3$ always denoting hydrogen:

| $R^1$ | $R^2$ | $R^1$ | $R^2$ |
|---|---|---|---|
| 4-$CF_3O$ | 5-Br | H | 4-$N(CF_3)_2$ |
| 4-$CF_3O$ | 5-Cl | H | 4-$CF_3SO_2$ |
| 4-$CF_3S$ | 5-Cl | 4-$CF_3$ | 6-$COOCH_3$ |
| 4-$CF_3$ | 5-$CF_3O$ | 4-$CF_3$ | 6-$COOC_2H_5$ |
| 3-$CF_3$ | 5-$CH_3$ | 4-$CF_3$ | 6-$COOiC_3H_7$ |
| 3-$CF_3$ | 5-Cl | 4-$CF_3$ | 6-$COOC_6H_5$ |
| 3-$CF_3$ | 5-Br | 4-$CF_3$ | 5-$COOCH_3$ |
| 3-$CF_3$ | 5-CN | 4-$CF_3$ | 5-$COOC_2H_5$ |
| 5-$CF_3S$ | 3-Br | 4-$CF_3$ | 5-$COOt.C_4H_9$ |
| 5-$CF_3$ | 3-CN | 5-$CF_3S$ | 3-Br |
| 3-$CF_3$ | 4-Cl | 5-$CF_3S$ | 3-Cl |
| 3-$CF_3O$ | 4-Cl | 5-$CF_3O$ | 3-$COOCH_3$ |
| 3-$CF_3$ | 4-CN | 5-$CF_3O$ | 3-$COOC_2H_5$ |
| 5-(2,6-di-chlor-4-tri-fluormethyl-phenoxy) | 3-Cl | 5-$CF_3O$ | 3-$COOiC_3H_7$ |
|  |  | 5-$CFClHCF_2S$ | 3-$COOCH_3$ |
|  |  | 5-$CFClHCF_2S$ | 3-$COOC_2H_5$ |
|  |  | 5-$CFClHCF_2S$ | 3-$COOiC_3H_7$ |
| 5-(2,6-di-chlor-4-tri-fluormethyl-phenoxy) | 4-Cl | 5-$CFClHCF_2S$ | 3-Br |
|  |  | 5-Hexafluor-propylthio | 3-Br |
| H | H | 3-$CF_3$ | 5-$COOC_4H_9$ |
| 4-Hexafluor-propoxy | 5-Cl | 5-$CF_3O$ | 3-$COOCH_3$ |
|  |  | 5-$CF_3O$ | 3-$COOC_4H_9$ |
| 5-$CF_3O$ | 3-$COOC_2H_5$ | 4-$CF_3CHFCF_2O$ | 5-$CF_3CHFCF_2O$ |
| 4-$CF_2HCF_2O$ | 5-$CF_2HCF_2O$ | 5-$CFClHCF_2O$ | 4-Cl |
| 4-$CFClHCF_2O$ | 5-$CFClHCF_2O$ | 5-$CF_3$ | 5-$CHFClCF_2O$ |
| 4-$CF_3$ | 5-$CF_3$—CHF—$CF_2O$ | 5-$CF_3SO_2$ | 3-Br |
| 4-$CF_3$ | 5-$CHFClCF_2O$ | 5-$CF_3SO_2$ | 3-Cl |

Further preferred compounds of the formula (I) have the formula (I')

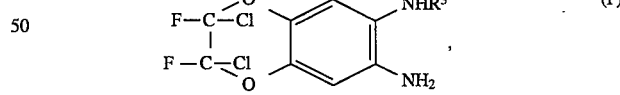

in which $R^3$ has the meaning given in formula (I).

Depending on the type of radicals $R^1$ and $R^2$, the compounds of the formula (I) can be prepared by different routes.

If compounds of the formula (I) in which not only $R^1$ but also $R^2$ is a donor group in the 4 and 5 position relative to the amino groups, for example compounds in which $R^1$ represents polyfluoroalkoxy or polyfluoroalkylthio and $R^1$ and/or $R^2$ represent fluorine, chlorine, bromine, alkyl, alkoxy or bis(fluoroalkyl)amino are to be prepared, a benzene derivative of the formula (II)

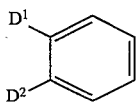

(II)

in which

D¹ represents $CF_3O$, $CF_3S$, $CHF_2CF_2O$, $CHFCl—CF_2O$, $CF_3CHFCF_2O$, $CF_3CF_2O$, $CF_3CF_2CF_2O$, $CF_3CF_2S$ or $CF_3CHFCF_2O$ and D² represents $CF_3O$, $CF_3S$, $CHF_2CF_2O$, $CHFCl—CF_2O$, $CF_3CHF—CF_2O$, $CF_3CF_2O$, $CF_3CF_2CF_2O$, $CF_3CF_2S$, $CF_3CHFCF_2O$, fluorine, chlorine, bromine, $C_1$–$C_6$-alkyl or $C_1$–$C_6$-alkoxy, can be dinitrated, the nitro groups can then be reduced to obtain compounds of the formula (I) in which $R^1$ and $R^2$ are in the 4 and 5 position relative to the amino groups and have the meaning of D¹ and D² (see formula (II)). Dinitration can be effected, for example, with $HNO_3/H_2SO_4$ mixtures, which, if desired, may also contain oleum, and at temperatures of, for example, 0° to 100° C. The reduction can be effected, for example, with iron in the presence of aqueous hydrochloric acid and ethanol at temperatures of, for example, 50° to 100° C. or catalytically with elemental hydrogen at, for example, 25° to 100° C., for example 1 to 100 bar, and in the presence of catalysts containing metals or metal compounds from subgroup VIII of the Periodic Table, in particular nickel or palladium.

If compounds of the formula (I) are to be prepared in which $R^1$ has the meaning given in formula (I) and is in the 4 position relative to the amino groups and $R^2$ represents Cl or Br in the 5 position relative to the amino groups, it is possible to react, for example, a nitrobenzene derivative of the formula (III)

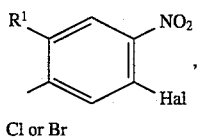

in which $R^1$ has the meaning given in formula (I) and Hal represents fluorine, chlorine or bromine, with ammonia, thus exchanging the Hal group for an amino group, and to reduce the nitroaniline thus obtained. Exchange of halogen for an amino group can be effected, for example, with liquid ammonia in the presence of water and a tetraalkylammonium salt at temperatures of, for example, 80° to 200° C. in a pressure vessel. Reduction of the nitroaniline can take place, for example, analogously to the reduction of dinitro compounds described above.

If compounds of the formula (I) in which $R^1$ has the meaning given in formula (I) and is in the 4 position relative to the amino groups, $R^2$ represents chlorine or bromine and is in the 6 position relative to the amino groups, and $R^3$ denotes hydrogen are to be prepared, it is possible to react, for example, a nitroaniline of the formula (IV)

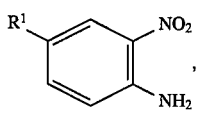

in which $R^1$ has the meaning given in formula (I), with a chlorinating or brominating agent, thus introducing a chlorine or bromine atom into the meta position relative to the nitro group, and then to reduce the nitro group. Suitable chlorinating or brominating agents are elemental chlorine, elemental bromine and other customary chlorinating and brominating agents. Examples of suitable solvents are water, dilute mineral acids, acetic acid, chloroalkanes and trifluoroacetic acid and examples of suitable temperatures are those from −20° to +50° C. Reduction can take place, for example, analogously to the reduction of dinitro compounds described above.

If compounds of the formula (I) in which $R^1$ is a donor group in the 4 position relative to the two amino groups, $R^2$ represents an acceptor group, for example $COO—C_1$–$C_6$-alkyl, CN, $CF_3$ or $SO_2—C_1$–$C_6$-alkyl, and $R_3$ is not hydrogen are to be prepared, it is possible, for example, to mononitrate a benzene derivative of the formula (V)

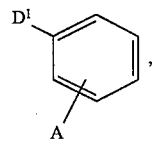

in which

D¹ has the meaning given in formula (II) and

A represents $CF_3$, $SO_2—C_1$–$C_6$-alkyl, which can be straight-chain or branched and be substituted completely or in part by fluorine, $COO—C_1$–$C_6$-alkyl or CN, ($NO_2$ group goes to the para position relative to D¹), reduce the $NO_2$ group to the $NH_2$ group, acylate the $NH_2$ group with, for example, acetic acid or trifluoroacetic acid, mononitrate again (this $NO_2$ group goes to the ortho position relative to the NHCOR groups where R is, for example, $CH_3$ or $CF_3$), reduce this $NO_2$ group to the $NH_2$ group, and, if it is desired to prepare a compound of the formula (I) where $R^3$ is hydrogen, eliminate the acyl group by hydrolysis.

The nitrations can be effected, for example, with nitric acid in a suitable organic solvent at temperatures of between, for example, 0° and 50° C., the reductions can be carried out, for example, analogously to the reductions of dinitro compounds described above, and the introduction and elimination of the acyl group, if it is to be carried out, can be carried out by methods customary for protecting amino groups.

In the process in which dinitration and reduction are carried out, it is surprising that the two nitro groups can be introduced into the ortho position relative to one another at a high selectivity and, despite the relatively drastic reaction conditions during dinitration, the fluoroalkoxy and fluoroalkylthio groups are not hydrolysed or eliminated.

In the process in which a halogen is exchanged for an $NH_2$ group by treatment with ammonia under pressure, it is surprising that selectively one halogen can be exchanged selectively in the ortho position relative to the $NO_2$ group.

Those o-phenylenediamines according to the invention containing fluoroalkyl(ene) groups in which $R^3$ denotes $COCH_3$ or $COCF_3$ can be converted by hydrolysis into o-phenylenediamines of the formula (I) where $R^3$ is hydrogen. o-Phenylenediamines of the formula (I) where $R^3$ is hydrogen or $COCF_3$ can be reacted to give substituted benzimidazoles of the formula

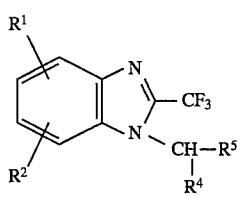

(VI)

by reacting substances of the formula (I) where $R^3$ is H or $COCF_3$ first with trifluoroacetic acid to give 2-trifluoromethylbenzimidazoles of the formula

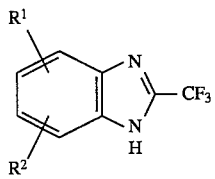

(VII)

and then carrying out a further reaction with compounds of the formula

(VIII)

$R^1$ and $R^2$ in formulae (VI), (VII) and (VIII) adopting the above range of meanings, $R^4$ representing hydrogen, alkyl, alkoxy or substituted or unsubstituted aryl, $R^5$ representing hydroxyl, cyano or alkyl, alkenyl, alkinyl, alkoxy, alkenyloxy, alkinyloxy, alkylthio, amino, aminocarbonyl, alkylcarbonyl, alkoxycarbonyl, alkylcarbonyloxy, dialkoxyphosphonyl, (hetero)aryl, (hetero)arylcarbonyl, (hetero)aryloxycarbonyl, (hetero)arylcarbonyloxy or (hetero)arylaminocarbonylaminocarbonyloxy, each of which is substituted or unsubstituted, and A denoting a suitable leaving group.

Leaving groups are known to one skilled in the art and examples thereof are halogen, alkyl-, alkoxy- or arylsulphonyloxy, hydroxyl or alkoxy.

Substituted benzimidazoles are active compounds for combating animal pests, arthropods and nematodes, in particular insects and arachnida, which occur in agriculture, in forests, in storage and material protection and in the hygiene sector.

EXAMPLES

Examples 1 to 6 (Dinitration and Reduction)

Example 1

320 g of 1,2-bis-(2-chloro-1,1,2-trifluoroethoxy)benzene were added dropwise to 500 g of a mixed acid containing 33% by weight of $HNO_3$ and 67% by weight of $H_2SO_4$. After one hour at 40° C., 250 ml of 20% strength by weight of oleum were added dropwise. The mixture was then heated to 80° C., and stirring was continued for 15 hours. A further 120 ml of 20% strength by weight of oleum and 250 g of the abovementioned mixed acid were then added dropwise. After 6 hours at 80° to 82° C., the mixture was cooled and poured onto ice. The organic phase was separated off and washed With water. Azeotropic drying with 1,2-dichloroethane gave 350 g of 98% by weight pure 1,2-dinitro-4,5-bis-(2-chloro-1,1,2-trifluoroethoxy)benzene (oil, $n_D^{20}$: 1.4832, GC 99.1%).

350 g Of this dinitro compound were added dropwise to a mixture of 1.5 l of ethanol, 50 ml of water, 30 ml of concentrated aqueous hydrochloric acid and 470 g of iron filings, and the mixture was refluxed for a total of 15 hours. The cooled solution was then filtered off, concentrated, and the residue was recrystallized from cyclohexane to give 216 g of 1,2-diamino-4,5-bis(2-chloro-1,1,2-trifluoroethoxy)-benzene of melting point 58° to 60° C.

Example 2

Analogously to Example 1, 1,2-bis-(1,1,2,3,3,3-hexafluoropropoxy)-benzene was reacted to give the corresponding 4,5-dinitro compound (oil, $n_D^{20}$: 1.4852) and the corresponding 4,5-diamino compound (oil, 87% by weight pure).

Example 3

Analogously to Example 1,1-(1,1,2-trifluoro-2-chloroethoxy)-2-chlorobenzene was reacted to give the corresponding 4,5-dinitro compound (melting point 56° to 57° C.) and the corresponding 4,5-diamino compound (melting point 67° to 68° C.).

Example 4

Analogously to Example 1, 1-trifluoromethoxy-2-bromobenzene was reacted to give the corresponding 4,5-dinitro compound (melting point 73° to 75° C.) and the corresponding 4,5-diamino compound (oil, 98% by weight pure, $n_D^{20}$: 1.5485).

Example 5

Analogously to Example 1, 1-trifluoromethoxy-2-chlorobenzene was reacted to give the corresponding 4,5-dinitro compound (melting point 55° to 56° C.) and the corresponding 4,5-diamino compound (melting point 56°–57° C.).

Example 6

1-(1,1,2,3,3,3-Hexafluoropropoxy)-2-chloro-benzene was reacted to give the corresponding 4,5-dinitro compound (oil) and the corresponding 4,5-diamino compound (oil).

Examples 7 to 12

Treatment with ammonia under pressure and reduction

Example 7

260 g of 3-nitro-2,5-dichlorobenzotrifluoride, 130 ml of water and 10 g of tetraethylammonium chloride were introduced into an autoclave as the initial charge, and 120 ml of liquid ammonia were injected. The mixture was then heated to 130° C. and stirred at this temperature for 10 hours. After cooling, the batch was filtered off, the removed precipitate washed with water and dried to give 194 g of 2-amino-3-nitro-5-chloro-benzotrifluoride of melting point 67° C.

134 g of the nitroaniline obtained as described above were dissolved in 800 ml of ethanol and 20 ml of water, 10 ml of concentrated aqueous hydrochloric acid and 160 g of iron filings were then added. The mixture was refluxed for 15 hours, then cooled, filtered off with suction, the filter residue was washed with dichloromethane, and the organic phases were then freed from the solvent under reduced pressure to give 171 g of 5-chloro-3-trifluoromethyl-1,2-diaminobenzene of melting point 53° C.

Example 8

Analogously to Example 7, 3-nitro-4,6-dichloro-difluoro-chloromethoxybenzene was reacted to give first 3-nitro-4-amino-6-chloro-difluorochloromethoxybenzene (melting point 73° C.), from which 3,4-diamino-6-chloro-difluoro-chloromethoxybenzene (oil) was obtained.

Example 9

Analogously to Example 7, 3-bromo-5-nitro-6-chlorobenzotrifluoride was reacted to give first 3-bromo-5-nitro-6-amino-benzotrifluoride (melting point 80° to 82° C.), from which 3-bromo-5,6-diamino-benzotrifluoride (melting point 52° to 54° C.) was prepared.

Example 10

Analogously to Example 7, 3-cyano-4-chloro-5-nitrobenzotrifluoride was reacted to give first 3-cyano-4-amino-5-nitro-benzotrifluoride (melting point 99° to 100° C.), from which 3-cyano-4,5-diamino-benzotrifluoride was prepared.

Example 11

Analogously to Example 7, 3,6-dichloro-5-nitro-benzotrifluoride was reacted to give first 3-chloro-5-nitro-6-amino-benzotrifluoride (melting point 53° to 54° C.), from which 3-chloro-5,6-diamino-benzotrifluoride was prepared.

Example 12

2-Bromo-4-fluoro-5-nitro-(1,1,2-trifluoro-2-chloro)ethoxybenzene was reacted to give first 2-bromo-4-amino-5-nitro-(1,1,2-trifluoro-2-chloro-ethoxy)-benzene (melting point 90° C.), from which 2-bromo-4,5-diamino-(1,1,2-trifluoro-2-chloro)-ethoxybenzene was prepared.

Example 13

(Halogenation of a Nitroaniline and Reduction)

24 g of finely powdered 2-nitro-4-trifluoromethylmercapto-aniline were dissolved in 50 ml of trifluoroacetic acid, and 18 g of bromine were metered in at 20° C. Stirring was then continued at 20° C. for 3 hours and at 40° C. for another 30 minutes, the mixture was poured into water, and the product taken up in dichloromethane to give, after removal of the solvent, 31 g of 6-bromo-2-nitro-4-trifluoromethylmercapto-aniline.

155 g of the nitroaniline thus prepared were refluxed in 700 ml of ethanol containing 15 ml of water, 10 ml of concentrated aqueous hydrochloric acid and 70 g of iron filings for 15 hours, the mixture was then filtered off, the filtrate was freed from the solvent under reduced pressure, and the solid crude product was recrystallized from cyclohexane to give 112 g of 6-bromo-4-trifluoromethylmercapto-1,2-diaminobenzene of melting point 60° to 61° C.

Example 14

Analogously to Example 13, 27 g of 2-nitro-4-trifluoromethylsulphonylaniline were brominated in 100 ml of acetic acid with 18 g of bromine.

Workup gave 32 g of 2-nitro-6-bromo-4-trifluoromethylsulphonyl-aniline, melting point 147° C.

32 g of the nitroamine thus prepared were reduced with iron filings in alcohol and aqueous hydrochloric acid to give 24 g of 3-bromo-5-trifluoromethylsulphonylphenylene-1,2-diamine, melting point 155°–157° C.

Example 15

Analogously to Example 14, 27 g of 2-nitro-4-trifluoromethylsulphonyl-aniline, were chlorinated in 100 ml acetic acid with 10 g of chlorine. This gave 29 g of 2-nitro-4-trifluoromethylsulphonyl-6-chloro-aniline, melting point: 138°–139° C.

Reduction gave 13 g of 3-chloro-5-trifluoromethylsulphonyl-1,2-phenylenediamine (melting point:143°–145° C.).

Example 16 to 20

(Nitration and Reduction in 2 Steps)

Example 16

263 g of 4-(2,6-dichloro-4-trifluoromethyl-phenoxy)acetanilide were dissolved in 1100 ml of dichloromethane, and the solution was introduced at 10° C. as the initial charge. 88 g of 98% strength by weight nitric acid were added dropwise at this temperature. Stirring was continued at 10° C. for 1 hour and at 30° C. for another 2 hours. After addition of 300ml of water, the phases were separated, and the organic phase was freed from dichloromethane under reduced pressure. 253 g of 2-nitro-4-(2,6-dichloro-4-trifluoromethyl-phenoxy)-acetanilide of melting point 138° to 140° C. remained.

91 g of the acetanilide thus prepared were dissolved in 800 ml of dioxane, 10 g of Raney nickel were added, and the mixture was hydrogenated at 25° to 45° C. in a hydrogenation apparatus at a maximum hydrogen pressure of 50 bar. After letdown and filtration, the dioxane was distilled off at a slight vacuum. 65 g of 2-amino-4-(2,6-dichloro-4-trifluoromethyl-phenoxy)-acetanilide of melting point 222° to 223° C. remained.

Example 17

Analogously to Example 16, 3-trifluoromethyl-4-methoxyacetanilide was reacted to give first 3-trifluoromethyl-4-methoxy-6-nitro-acetanilide (melting point 143° to 144° C.), from which 3-trifluoromethyl-4-methoxy-6-aminoacetanilide (melting point 164° to 165° C.) was prepared.

Example 18

Analogously to Example 16, 3-trifluoromethyl-4-fluorotrifluoroacetanilide was reacted to give first 3-trifluoromethyl-4-fluoro-6-nitro-trifluoroacetanilide (melting point 78° C.), from which 3-trifluoromethyl-4-fluoro-6-aminotrifluoroacetanilide (melting point 92° to 93° C.) was prepared.

Example 19

Analogously to Example 16, 3-trifluoromethyl-4-bromotrifluoroacetanilide was reinacted to give first 3-trifluoromethyl-4-bromo-6-nitro-trifluoroacetanilide (melting point 110° to 112° C.), from which 3-trifluoromethyl-4-bromo-6-amino-trifluoroacetanilide (melting point 63° to 65° C.) was prepared.

Example 20

Analogously to Example 16, 3-trifluoromethylthio-4-chloro-trifluoroacetanilide was reacted to give first 3-trifluoromethylthio-4-chloro-6-nitro-trifluoroacetanilide (melting point 99°–100° C.), from which 3-trifluoromethylthio-4-chloro-6-aminotrifluoroacetanilide (melting point: 88°–90° C.) was prepared.

Example 21

0.2 mol of 3-bromo-5-trifluoromethyl-phenylene-1,2-diamine was refluxed together with 150 ml of trifluoroacetic acid for 3 hours. For workup, excess trifluoroacetic acid was distilled off, and the residue was distributed between 100 ml of water and 300 ml of ethyl acetate. The organic phase was separated off, washed in succession with 100 ml each of aqueous sodium bicarbonate solution and water, dried over sodium sulphate and concentrated in vacuo. The residue was purified by chromatography on silica gel (eluent: 1:1 cyclohexane/ethyl acetate).

This gave 4-bromo-[-trifluoromethyl-2-trifluoromethyl-1H-benzimidazole of melting point 149°–151° C.

Example 22

0.03 mol of 4-bromo-6-trifluoromethyl-2-trifluoromethyl-1H-benzimidazole and 0.06 mol of powdered potassium carbonate were refluxed in 70 ml of ethyl acetate for 15 minutes, 3.9 g (0.04 mol) of chloromethyl methyl thioether in 20 ml of ethyl acetate were then added, and the mixture was refluxed for another 4 hours with stirring. For workup, the cooled reaction mixture was washed twice with 40 ml each of water, dried over sodium sulphate, concentrated in vacuo, and the residue was purified by chromatography on silica gel (eluent: dichloromethane).

This gave 1-methylthiomethyl-4-bromo-6-trifluoromethyl-2-trifluoromethyl-benzimidazole of melting point 56°–60° C.

Example 23 a) 125 g of mixed acid (33% of nitric acid, 67% of sulphuric acid) were added dropwise at 20° C. to 157 g of 2-(2H-hexafluoropropoxy)isopropylbenzene. After 2 hours of stirring at 20° to 25° C. the batch was poured onto ice, and the organic phase was then extracted with methyl tert.-butyl ether. Fine distillation of the extracted organic phase gave 89 g of 2-(2H-hexafluoropropoxy)-5-nitro-isopropylbenzene (boiling point: 142°–145° C./20 mbar; $n_D^{20}$: 1.4562).

b) A mixture of 89 g of 2-(2H-hexafluoropropoxy)-5-nitro-isopropylbenzene, 5 ml of 35% strength aqueous hydrochloric acid, 3 ml of water, 80 g of iron powder and 420 ml of ethanol was refluxed for 15 hours, 4 g of sodium hydroxide were then added, and the reaction mixture was filtered while hot. The filtration residue was washed with ethanol, and the filtrate was then distilled together with the ethanolic extract to give 53 g of 3-isopropyl-4-(2H-hexafluoropropoxy)-aniline (boiling point:110°–115° C./12 mbar).

c) 30 g of 3-isopropyl-4-(2H-hexafluoropropoxy)aniline were introduced as the initial charge into 150 ml of toluene, and a mixture of 40 g of trifluoroacetic anhydride and 50 ml of trifluoroacetic acid was then added dropwise. The mixture was then refluxed for 6 hours, cooled, and the slightly volatile components were distilled off at 15 mbar. The remaining residue was distilled in a high vacuum. Yield: 28 g of 3-isopropyl-4-(2H-hexafluoropropoxy)-N-trifluoroacetanilide (boiling point: 110°–120° C./0.15 mbar).

d) 18 g of 3-isopropyl-4-(2H-hexafluoropropoxy)trifluoroacetanilide and 50 ml of dichloromethane were introduced as the initial charge, and 26 g of mixed acid (33% of nitric acid, 67% of sulphuric acid) were then added dropwise at 20° C. After 5 hours of stirring at 20°–25° C. 60 g of ice were added, the phases were separated, and the organic phase was concentrated. 19 g of a solid remained which was reacted without any further purification.

e) 19 g of the 2-nitro-3-isopropyl-4-(2H-hexafluoropropoxy)-trifluoroacetanilide obtained according to d) were refluxed together with 7 g of iron powder, 7 g of iron filings, 1.5 ml of hydrochloric acid and 70 ml of ethanol for 20 hours. The mixture was then filtered while hot, the filter residue was washed with ethanol, and the filtrate and the ethanolic solution were then combined and freed from the solvent. After cooling, the resulting residue was covered with a layer of n-hexane and triturated. After standing overnight, the liquid was decanted, and the remaining solid product analyzed. It consisted of 11 g of 2-amino-3-isopropyl-4-(2H-hexafluoropropoxy)-trifluoroacetanilide of melting point 167°–168° C. which was 95.5% pure as determined by gas chromatography.

What is claimed is:

1. o-Phenylenediamines containing a fluoroalkylene group of the formula (I')

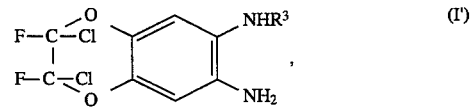

in which $R^3$ represents hydrogen, $COCH_3$ or $COCF_3$.

* * * * *